United States Patent [19]

Johnston

[11] 4,094,303

[45] June 13, 1978

[54] TYMPANIC MEMBRANE VENT

[75] Inventor: Douglas W. Johnston, Longwood, Fla.

[73] Assignee: Glasrock Products, Inc., Atlanta, Ga.

[21] Appl. No.: 769,398

[22] Filed: Feb. 16, 1977

[51] Int. Cl.² .................... A61B 19/00; A61F 1/18
[52] U.S. Cl. ............................ 128/1 R; 3/1; 128/151
[58] Field of Search ............ 128/1 R, 151, 350 R, 128/350 V; 3/1, 1.9

[56] References Cited

U.S. PATENT DOCUMENTS 3,807,409  4/1974  Paparella et al. ............... 128/350 R
3,916,873  11/1975  Wasserman ....................... 128/1 R

FOREIGN PATENT DOCUMENTS 947,903  5/1974  Canada ............................ 128/350 R Primary Examiner—Ronald L. Frinks
Attorney, Agent, or Firm—Lane, Aitken, Dunner & Ziems

[57] ABSTRACT

The middle ear space is vented through the tympanic membrane by a piece of porous plastic material positioned to extend through the tympanic membrane. The pore size is in the range of 5 to 25 micrometers in diameter to effectively prevent water passage and permit tissue ingrowth a few pores deep from the tympanic membrane into the side walls of the vent. The vent is generally cylindrical in shape provided with a section of reduced cross-sectional area intermediate its ends, which section engages the tympanic membrane when the vent is in position.

10 Claims, 5 Drawing Figures

TYMPANIC MEMBRANE VENT

This invention relates to a device for venting the middle ear through the tympanic membrane.

In the treatment of retracted tympanic membranes and serious otitis media and/or Eustachian tube malfunction, a small ventilation tube is sometimes inserted through the tympanic membrane to allow the passage of air into the middle ear space to relieve negative pressure buildup in the middle ear. A disadvantage of this technique, which has been used for over twenty years, is that the tube will allow the passage of water as well as air and bacteria. When the patient gets water into his ear, as frequently happens with swimming or bathing, the water can pass through the tube and into the middle ear space. If even a small drop of water gets into the middle ear, infection can rapidly ensue resulting in accute otitis media, a draining ear, and extrusion of the tube.

SUMMARY OF THE PRESENT INVENTION

In accordance with the present invention, this problem with the prior art technique of treatment is overcome by permitting air passage through the tympanic membrane but not water passage. This is achieved by means of a vent comprising an elongated piece of porous plastic material, which is shaped to pass through and be held in place in the tympanic membrane like the tubes of the prior art. The pores of the porous plastic material are interconnected so that air can pass through the interconnected pores from the ear canal into the middle ear space. The plastic material is hydrophobic so that water is effectively prevented from being transmitted through the vent even through water may get into the ear canal and come into contact with the porous plastic material. The vent is made porous throughout so that its porosity extends to the sidewall of the device, which comes in contact with the tympanic membrane. The pore size of the device is selected to permit tissue ingrowth, in the form of collagen fibers, into the sidewall of the device. This tissue ingrowth helps hold the device in place to prevent extrusion. The pore size is selected to be small enough so as to limit the tissue ingrowth to just a few pores deep into the sidewall of the device both to facilitate later removal and also to avoid the possibility of the tissue ingrowth closing off the vent.

DESCRIPTION OF THE PREFERRED EMBODIMENTS

Figure 1:
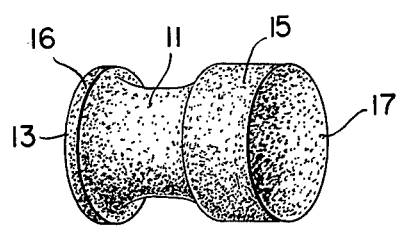
FIG. 1 illustrates a perspective view of one embodiment of the vent of the present invention.

As shown in FIG. 1, the vent of the present invention comprises a generally cylindrical piece of porous material having an axial length greater than its diameter. The sidewall of the device is a surface of revolution having a filleted neck 11 of reduced diameter near its inner end 13, which is designed to be contiguous with the middle ear space, leaving larger diameter portions 15 and 16 on opposite sides of the neck 11. The neck 11 extends over about half the length of the device. The enlarged section 15, which is at the outer end of the device designed to extend into the ear canal, is cylindrical and is about the same length as the neck 11.

The diameter of the device is about 3 millimeters and the axial length of the device is about 4 millimeters. The neck 11 extends over about two millimeters of the length as does the cylindrical section 15. The cylindrical section 15 should be long enough to facilitate grasping with forceps. The diameter of the neck 11 is reduced at the middle to about 2.5 millimeters. The enlarged section 16 may have a short axial cylindrical length of $\frac{1}{2}$ millimeter or less to ensure that the porous material at the edge of the device is sufficiently strong to maintain its structural integrity.

The device is made out of a single piece of porous material, which is hydrophobic and which should remain chemically and physically stable when in use. These requirements are satisfied by most common hydrophobic plastics. "Plastic" as used herein is defined as encompassing synthetic resins generally including thermoplastic, thermosetting resins as well as elastomeric materials. A preferred material is polytetrafluoroethylene, which is sold under the name "Teflon." Alternatively, the device may be made of polyvinyldiene fluoride, which is sold under the name "Kynar." Both Kynar and Teflon are fluorocarbons. In addition, polyolefins, such as polyethylene or polypropylene, could be used. Instead of using the above described naturally hydrophobic materials, a nonhydrophobic material, such as nylon, may be used if it is treated with a nonwetting material, such as silicone, to make the material hydrophobic. The phrase "hydrophobic material" as used herein is defined as meaning either a material which is naturally hydrophobic or a material which is not naturally hydrophobic but which has been treated to make it hydrophobic. The pores of the material are interconnecting so as to permit air passage through the pores of the device from one end to the other. The pore size should be in the range of 5 to 25 micrometers in diameter. The porous plastic material may be made by the method described in U.S. Pat. No. 3,896,196.

Figure 2:
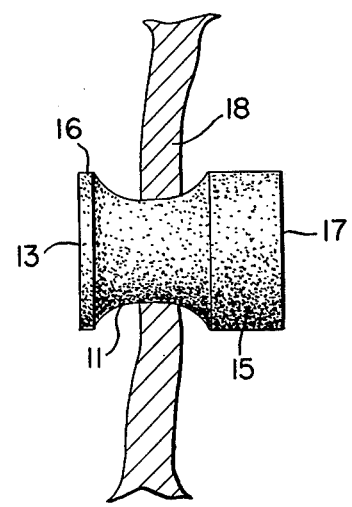
FIG. 2 is a sectional view taken through the tympanic membrane and illustrating the vent of FIG. 1 in place in the tympanic membrane.

FIG. 2 illustrates the device in FIG. 1 in place in the tympanic membrane 18. As shown in FIG. 2, the device is positioned with the inner end 13 inside the middle ear space and the outer end 17 extending into the ear canal with the tympanic membrane contacting the device in the neck 11. Initially the enlarged diameter portions 15 and 16 on each side of the neck 11 will hold the vent in position. After the device has been inserted, collagen fibers from the tympanic membrane will grow into the pores of the sidewalls of the neck 11 to secure the vent in position. The pore size is important to permit only a limited tissue ingrowth. The pores preferably should be large enough so that some tissue ingrowth in the form of collagen fibers will occur in the sidewalls of the device to help secure the device in the tympanic membrane and prevent the device from being extruded. The pore size preferably should be small enough so that this tissue ingrowth is limited to no more than a few pores deep into the device to facilitate later removal of the vent. As a minimum, the pore size preferably should be small enough to limit the tissue ingrowth and prevent it from extending all the way through the device and closing off the air passage. The pore size also should be small enough so that the device will not transmit water in contact therewith in the ear canal under pressure normally expected to be encountered by the patient and, accordingly, must at least be small enough so that the hydrophobicity of the material will prevent passage of water under atmospheric pressure. These objectives are accomplished by making the pore size in the range of 5 to 25 micrometers in diameter.

Figure 3:
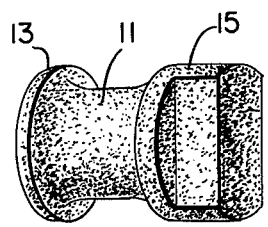
FIGS. 3-5 illustrate alternative embodiments of the vent of the present invention.
Figure 4:
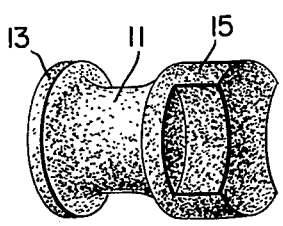
Figure 5:
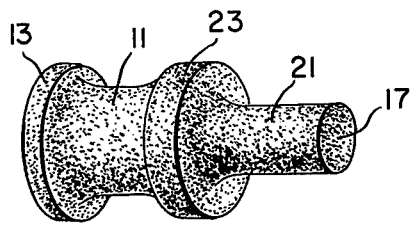

Alternative shapes for the device are shown in FIGS. 3-5. As shown in FIG. 3, the cylindrical portion 15 has cut out segments to facilitate grasping the portion 15 with forceps for handling of the device. The embodiment of FIG. 4 is similar to that shown in FIG. 3 except that the cutout segments in the enlarged cylindrical section 15 define arcuate surfaces to be engaged by the forceps instead of flat surfaces.

In the embodiment shown in FIG. 5, the outer end 17 of the device is shaped to have a reduced diameter section 21 to facilitate grasping the outer end of the device with forceps. A short cylindrical section 23 of enlarged diameter is provided between the neck 11 and the section 21 of reduced diameter. The section 23 has the same outside diameter of about 3 millimeters as the section 15 in the embodiment of FIG. 1 and, like the section 15, serves to initially maintain the device in place after it has been inserted in the tympanic membrane.

While the preferred shape of the device is generally cylindrical as shown in each of the embodiments, different shapes such as ones with a square, rectangular, or eliptical cross-section would be operable. These and many other modifications may be made to the above described preferred embodiments of the invention without departing from the spirit and scope of the invention, which is defined in the appended claims.

I claim:

1. A tympanic membrane vent comprising a piece of porous hydrophobic material having pores therein and of a size and shape to be inserted through and held in place extending through the tympanic membrane of the human ear, said piece having a first end surface adapted to be positioned in the middle ear space, a second end surface adapted to be positioned in the ear canal, and exterior side surfaces extending between said end surfaces adapted to engage the tympanic membrane when said piece is in place extending through the tympanic membrane, said end surfaces and said side surfaces defining a closed three-dimensional volume, the interior enclosed by said end surfaces and said side surfaces being filled with said porous material, said pores being interconnected to permit air passage through said interconnected pores between the ear canal and the middle ear space when said piece is in place extending through the tympanic membrane, said pores having a size small enough so that the hydrophobicity of the material prevents passage of water therethrough from the ear canal into the middle ear space when water under atmospheric pressure in said ear canal comes in contact with said piece.

2. A tympanic membrane vent as recited in claim 1, wherein said porous hydrophobic material is a plastic.

3. A tympanic membrane vent as recited in claim 2, wherein said plastic is polytetrafluoroetylene.

4. A tympanic membrane vent as recited in claim 1, wherein said piece has an elongated shape.

5. A tympanic membrane vent as recited in claim 1, wherein said piece has a section of reduced cross-sectional area intermediate to opposite ends thereof between sections of larger cross-sectional area.

6. A tympanic membrane vent as recited in claim 5, wherein said section of reduced cross-sectional area is nearer to one of said opposite ends than the other.

7. A tympanic membrane vent as recited in claim 6, wherein said other end is provided with means to facilitate grasping thereof by forceps.

8. A tympanic membrane vent comprising a piece of porous hydrophobic material having pores therein and of a size and shape to be inserted through and held in place extending through the tympanic membrane of the human ear, said pores being interconnected to permit air passage through said interconnected pores between the ear canal and the middle ear space when said piece is in place extending through the tympanic membrane, said pores having a size small enough so that the hydrophobicity of the material prevents passage of water therethrough from the ear canal into the middle ear space when water under atmospheric pressure in said ear canal comes in contact with said piece, said pore size being selected to permit tissue ingrowth from said tympanic membrane into the sidewalls of said vent but limit the depth of tissue ingrowth so as to prevent closing off the ear vent by tissue ingrowth.

9. A tympanic membrane vent as recited in claim 8, wherein said pore size is from 5 to 25 micrometers in diameter.

10. A method of venting the middle ear space comprising inserting a piece of porous hydrophobic material through the tympanic membrane, the porous material having interconnected pores to permit passage of air through said piece of material when in place extending through the tympanic membrane, the pore size being small enough so that the hydrophobicity of the material effectively prevents water passage from the ear canal into the middle ear space through said piece of material when in place extending through the tympanic membrane and contacted by water under atmospheric pressure in the ear canal and being selected to permit tissue ingrowth from said tympanic membrane into the sidewalls of said piece but limit the depth of tissue ingrowth so as to prevent closing off the ear vent by tissue ingrowth.

* * * * *